United States Patent [19]

Pawlikowski

[11] Patent Number: 4,929,231
[45] Date of Patent: May 29, 1990

[54] NON-REUSABLE HYPODERMIC SYRINGE

[76] Inventor: Mark A. Pawlikowski, Box 101D Wolf Neck Rd., Stonington, Conn. 06378

[21] Appl. No.: 305,708

[22] Filed: Feb. 2, 1989

[51] Int. Cl.⁵ .............................................. A61M 5/00
[52] U.S. Cl. ..................................... 604/110; 604/221
[58] Field of Search ............... 604/110, 187, 218, 228, 604/221, 222

[56] References Cited

U.S. PATENT DOCUMENTS

| | | | |
|---|---|---|---|
| 4,391,272 | 7/1983 | Staempfli | 604/110 |
| 4,493,703 | 1/1985 | Butterfield | 604/110 |
| 4,713,056 | 12/1987 | Butterfield | 604/110 |

Primary Examiner—John D. Yasko
Attorney, Agent, or Firm—Richard A. Craig

[57] ABSTRACT

A non-reusable hypodermic syringe includes a body having a front end, a rear end and an inner wall extending from the front end to the rear end, a needle extending from the front end. A plunger assembly includes a rod member having a rearward end extending from the rear end of the body and a forward end within the body and a head portion integral with the forward end of the rod member. The head portion has an outwardly facing circumferential groove therearound. An O-ring is seated in and protrudes outwardly from the outwardly facing groove and engages the inner wall of the body. The body has an inwardly facing circumferential groove adjacent the front end of the body and positioned to receive the O-ring therein when the grooves confront each other, thereafter to resist movement of the rod member in the filling direction away from the front end of the body, thereby rendering the syringe non-reusable. A deflectable cap is affixed to the face of the head member or is seated in the front end of the body. The cap is deflectable as the grooves approach each other, so that a user can sense a change in the syringe action and realize that slight further movement of the rod member toward the front end wall achieve non-reusability.

7 Claims, 2 Drawing Sheets

U.S. Patent    May 29, 1990    Sheet 2 of 2    4,929,231
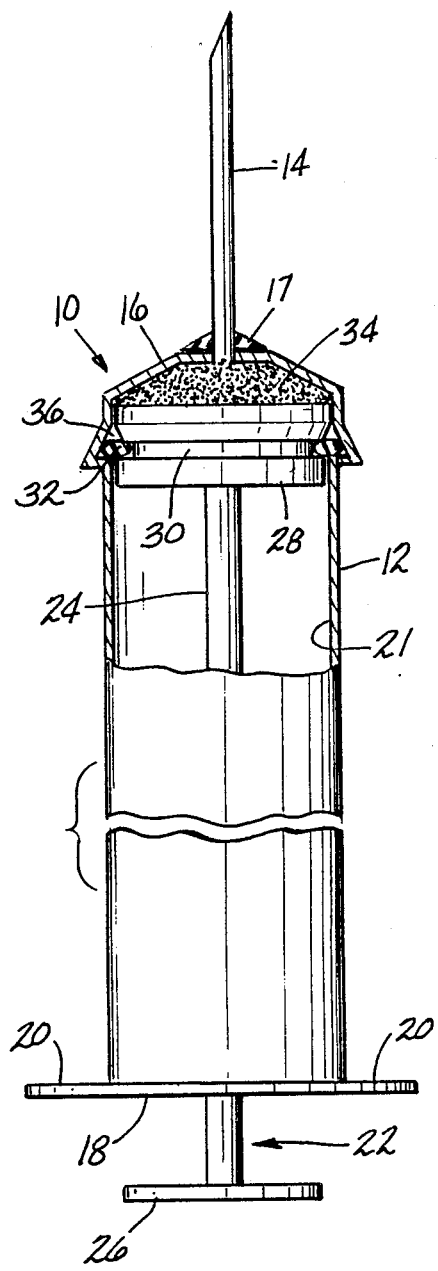
FIG-3
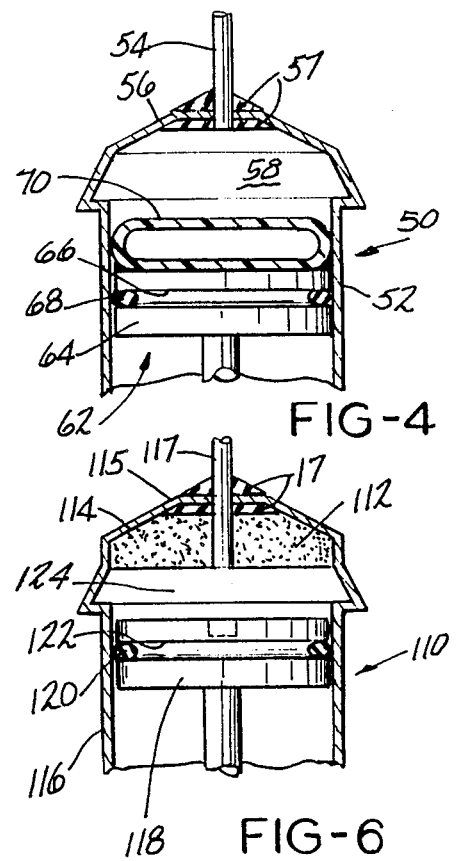
FIG-4
FIG-6
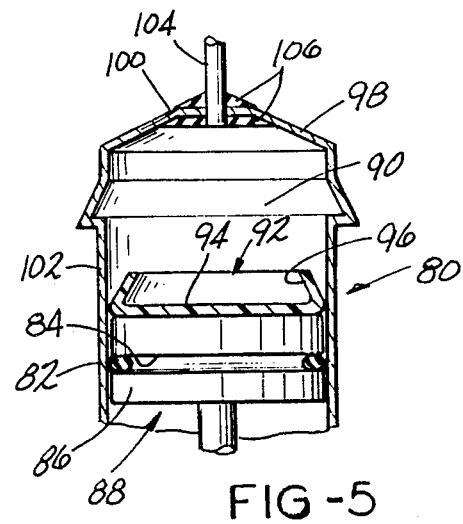
FIG-5

NON-REUSABLE HYPODERMIC SYRINGE

BACKGROUND OF THE INVENTION

This invention relates to hypodermic syringes and more particularly to a hypodermic syringe which is non-reusable.

Typical prior art hypodermic syringes are physically reusable, i.e., they are manipulatable between loaded and unloaded positions an indefinite number of times, requiring medical personnel to physically break off the needle at great personal risk. In today's AIDS climate, and for other reasons, this is highly undesirable.

It is therefore an important object of the invention to provide a non-reusable hypodermic syringe, so that the administrator of the medication need not go near the needle to render the syringe non-reusable and can safely discard the syringe with greatly reduced personal risk.

It is another object of the invention to provide a non-reusable hypodermic syringe of simple, inexpensive and reliable construction. Other objects and advantages of the invention will appear hereinafter.

SUMMARY OF THE INVENTION

The invention provides a non-reusable hypodermic syringe which includes a body having a front end, a rear end and an inner wall extending from the front end to the rear end, and a needle extending from the front end of the body. A plunger assembly includes a rod member having a rearward end extending from the rear end of the body and a forward end within the body and a head portion integral with the forward end of the rod member and having an outwardly facing circumferential groove therearound. An O-ring is seated in and protrudes outwardly from the outwardly facing groove and engages the inner wall of the body. The body has an inwardly facing circumferential groove adjacent the front end of the body and positioned to receive the O-ring therein when the grooves confront each other, thereafter to resist movement of the rod member in the filling direction away from the front end of the body, thereby rendering the syringe non-reusable. A deflectable cap is affixed to the face of the head portion or is seated in the front end of the body. The cap is deflectable as the grooves approach each other, so that a user can sense a change in the syringe action and realize that slight further movement of the rod member toward the front end will achieve non-reusability. It is important for the user to sense that slight further movement of the rod member toward the front end will achieve non-reusability in order to establish a zero filled position without accidentally passing therethrough to the locked position.

The inwardly facing groove has a plane surface confronting the front end of the syringe body and perpendicular to the axis of the body and a frusto-conical surface making an acute angle with the plane surface and intersecting the plane surface at its radially outer periphery.

DESCRIPTION OF THE DRAWING

FIG. 3 is a view similar to FIG. 2 but showing the parts in their finally occupied, locked, non-reusable positions; and FIGS. 4, 5 and 6 are fragmentary axial sectional views of the front end of the syringe body of each of second, third and fourth preferred embodiments of the invention, respectively, with the parts positioned substantially as in FIG. 2.

DESCRIPTION OF THE INVENTION

Figure 1:
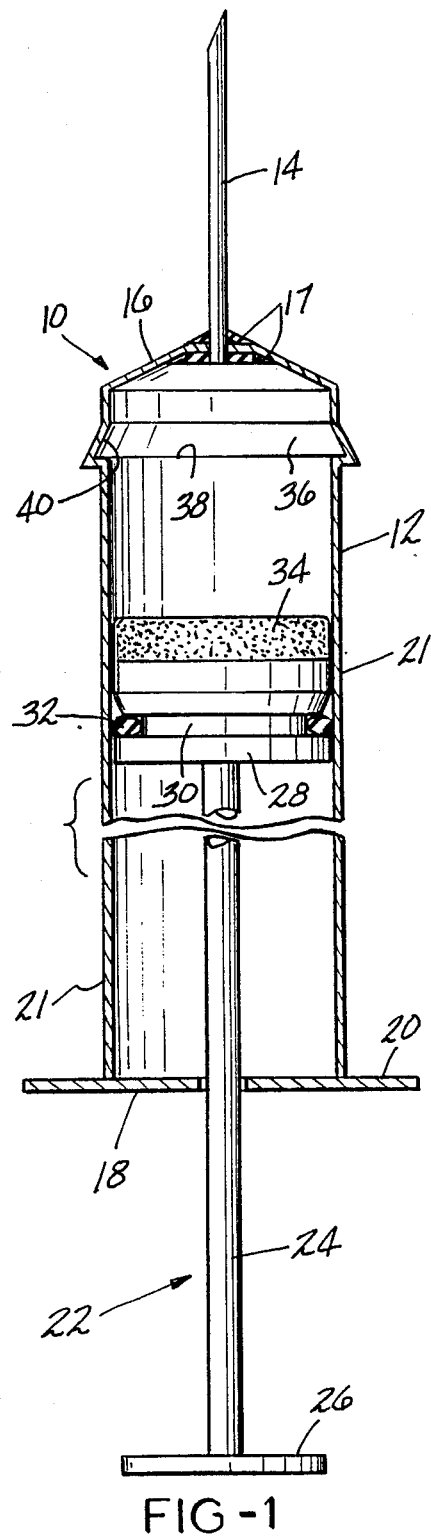
FIG. 1 is a fragmentary axial sectional view of a nonreusable hypodermic syringe which is a first preferred embodiment of the invention, showing the parts in the relative positions occupied at the start of an injection and end of manufacturing or shipping state, to prevent locking during transport and handling.

The invention will be described first with reference to FIGS. 1–3 which show a non-reusable hypodermic syringe 10 which comprises a syringe body 12 and a needle 14 extending from a front end 16 of body 12, needle 14 being sealed at front end 16 as indicated at 17. Body 12 is generally cylindrical and needle 14 is coaxial with body 12. Body 12 also has a rear end 18 with an external finger flange 20. Front end 16 is internally frusto-conical, and an inner wall 21 extends from front end 16 to rear end 18.

Syringe 10 also comprises a plunger assembly 22 which includes a rod member 24 which lies on the axis of body 12 and extends from rear end 18 of body 12 and has at its rearward end a thumb-engaging radial enlargement 26.

The forward end of rod member 24 is within body 12 and confronts front end 16 thereof and has an integral head portion 28 which has telescoping fit within body 12. Head portion 28 has an outwardly facing circumferential groove 30 seated in which is an O-ring 32. O-ring 32 protrudes outwardly from groove 30 and slidably engages the inner wall of body 12. Head portion 28 has, affixed to its face confronting front end 16 of body 12, a deflectable cap 34, a suitable material for which is SBR, natural rubber and the like or thermoplastic elastomers such as SBS block polymers, EP copolymers, PP modified EPDM/EPR and the like. Cap 34 is normally disc-shaped, as shown in FIGS. 1 and 2, but is deflectable to frusto-conical shape when it engages front end 16, as shown in FIG. 3. Cap 34 before deflection has the same outside diameter as head portion 28.

Adjacent front end 16 of body 12, the inner wall of body 12 is provided with an inwardly facing circumferential groove 36. Groove 36 has a plane surface 38 confronting front end 16 of body 12 and perpendicular to the axis of body 12. Groove 36 has a frusto-conical surface 40 which makes an acute angle of roughly 60–70 degrees with surface 38 and which intersects plane surface 38 at the radially outer periphery thereof.

Figure 2:
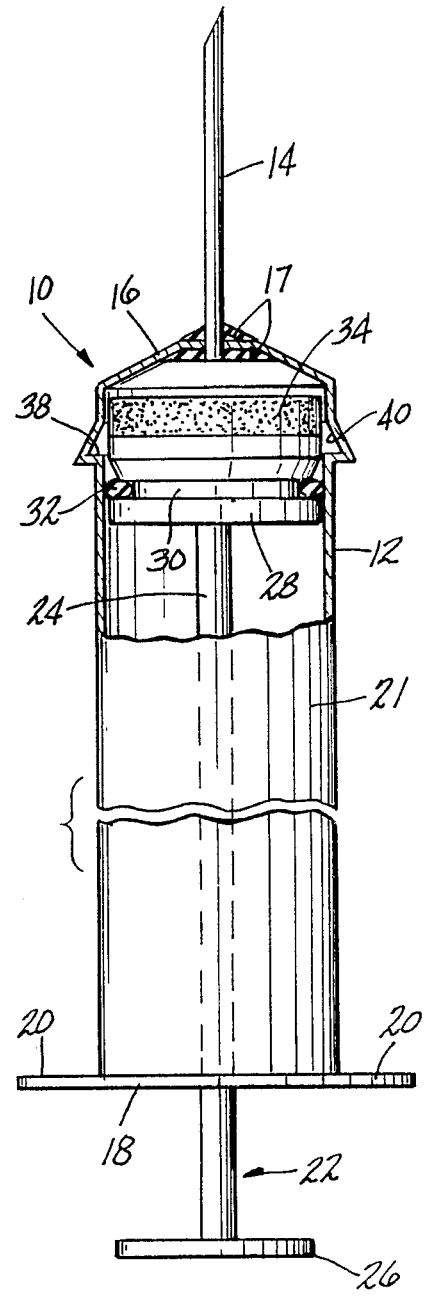
FIG. 2 is a view similar to FIG. 1 but showing the parts in the relative positions occupied almost at the conclusion of an injection.

As stated, FIG. 1 shows the parts of syringe 10 at the start of an injection, whereas FIG. 2 shows theparts substantially at the conclusion of the injection. In FIG. 2, deflectable cap 34 has just engaged front end 16 of body 12 and has not started to deflect, and groove 30 and O-ring 32 are just short of reaching groove 36.

Upon further travel of rod member 24 toward front end 16 of body 12, the administrator of the injection will sense a change in the action of syringe 10, due to deformation of deflectable member 34 and will know that he or she must go a little further in order to cause O-ring 32 to snap into groove 36, thus to inject all the required medication and achieve the desired locking and non-reusability of syringe 10.

Before O-ring 32 snaps into groove 36, it is under radial compression applied to it by inner wall 21. When O-ring 32 reaches groove 36, the radial compression is at least partly relieved. This causes O-ring 32 to snap radially outwardly into groove 36, thereafter to resist any effort to move rod member 24 in the direction away from front end 16 of body 12, by reason of the overlapping engagement of O-ring 32 with surface 38 of groove 36. Effectively, this renders syringe 10 non-reusable, as desired.

FIG. 4 is a fragmentary sectional view of a second preferred non-reusable syringe 50 embodying the invention, with the parts illustrated in the relative positions occupied almost at the conclusion of an injection. Syringe 50 includes a syringe body 52 with a needle 54 extending from a front end 56, where needle 54 is sealed as indicated at 57. Body 52 is generally cylindrical and is coaxial with needle 54. Front end 56 is internally frusto-conical, and body 52 has an internal circumferential groove 58 like groove 36 of body 12. Syringe 50 also comprises a plunger assembly 62 having a head portion 64 with a sharp sided outwardly facing circumferential groove 66 therearound, and an O-ring 68 seated in groove 66 and projecting outwardly therefrom into engagement with the inner wall of body 52. Plunger assembly 62 also includes a deflectable cap 70 (which may be of the same material as cap 34) in the form of a rubber-like hollow pillow affixed to the face of head portion 64 and which is deflectable by engagement with the frusto-conical interior of front end 56 of body 52 as O-ring 68 approaches groove 58, before O-ring 68 snaps into groove 58 to render syringe 50 non-reusable.

FIG. 5 is a fragmentary sectional view of a third preferred non-reusable syringe 80 which is quite similar to syringe 50, syringe 80 having an O-ring 82 in a sharp-sided groove 84 in a head portion 86 of a plunger assembly 88. O-ring 82 snaps into a groove 90 which is like groove 58 of syringe 50. A deflectable cap 92 (which may be of the same material as cap 34) is in the form of a rubber-like dished member having a solid base 94 affixed to the face of head portion 86 and a circumferentially continuous deflectable flange 96 which is deflectable by engagement with a frusto-conical portion 98 at a front end 100 of a syringe body 102, as O-ring 82 approaches groove 90, before O-ring 82 snaps into groove 90 to render syringe 80 non-reusable. A needle 104 extends from front end 100, where needle 104 is sealed as indicated at 106.

FIG. 6 is a fragmentary sectional view of a fourth preferred non-reusable syringe 110 which is quite similar to syringe 10, except that syringe 110 includes a deflectable cap 112 (which may be of the same material as cap 34) which is affixed within a frusto-conical portion 114 at a front end 115 of a body 116. A needle 117 passes axially through front end 115 of body 116 and axially through cap 112, and cap 112 is deflectable by the plane face of head portion 118 which carries an O-ring 120 in a sharp sided groove 122. Head portion 118 engages and starts to deflect cap 112 before O-ring 120 snaps into a groove 124 in body 116 to render syringe 110 non-reusable.

It is apparent that the invention achieves the stated objects and advantages and others.

The disclosed details are exemplary only and are not to be taken as limitations on the invention except as those details may be includes in the appended claims.

What is claimed is:

1. A non-reusable hypodermic syringe comprising a syringe body having a front end, a rear end and an inner wall extending from said front end to said rear end, a needle extending from said front end, and a plunger assembly including a rod member having a rearward end extending from said rear end of said body and a forward end within said body and a head portion integral with said forward end of said rod member and having an outwardly facing circumferential groove and an O-ring seated in and protruding outwardly therefrom and engaging said inner wall of said body, said body having an inwardly facing circumferential groove adjacent said front end of said body and positioned to receive said O-ring therein when said grooves confront each other, thereafter to resist movement of said rod member in the direction away from said front end of said body and render said syringe non-reusable, said syringe further comprising a deflectable cap affixed to the face of said head portion confronting said front end of said body, said cap being subject to deflection by said front end as said outwardly facing circumferential groove approaches said inwardly facing circumferential groove, such that an administrator of an injection will sense a change in the action of said syringe and know that slight further movement of said rod member toward said front end will bring said grooves into radial alignment.

2. A non-reusable hypodermic syringe comprising a syringe, a body having a front end, a rear end and an inner wall extending from said front end to said rear end, a needle extending from said front end, and a plunger assembly including a rod member having a rearward end extending from said rear end of said body and a forward end within said body and a head portion integral with said forward end of said rod member and having an outwardly facing circumferential groove and an O-ring seated in and protruding outwardly therefrom and engaging said inner wall of said body, said body having an inwardly facing circumferential groove adjacent said front end of said body and positioned to receive said O-ring therein when said grooves confront each other, thereafter to resist movement of said rod member in the direction away from said front end of said body and render said syringe non-reusable, wherein said inwardly facing groove has a plane surface confronting said front end and perpendicular to the axis of said body and a frusto-conical surface making an acute angle with said plane surface and intersecting said plane surface at its radially outer periphery.

3. A syringe according to claim 1 wherein said deflectable cap is normally disc-shaped and said front end of said body is internally frusto-conical, whereby said deflectable cap is deflectable to frusto-conical shape by said front end of said body.

4. A syringe according to claim 1 wherein said deflectable cap is a rubber-like hollow pillow.

5. A syringe according to claim 1 wherein said deflectable cap is a rubber-like dished member having a solid base and a deflectable flange upstanding from the outer periphery of said base.

6. A syringe according to claim 5 wherein said deflectable flange is circumferentially continuous.

7. A non-reusable hypodermic syringe comprising a syringe body having a front end, a rear end and an inner wall extending from said front end to said rear end, a needle extending from said front end, and a plunger assembly including a rod member having a rearward end extending from said rear end of said body and a forward end within said body and a head portion integral with said forward end of said rod member and having an outwardly facing circumferential groove and an O-ring seated in and protruding outwardly therefrom and engaging said inner wall of said body, said body having an inwardly facing circumferential groove adjacent said front end of said body and positioned to receive said O-ring therein when said grooves confront each other, thereafter to resist movement of said rod member in the direction away from said front end of said body and render said syringe non-reusable, said syringe further comprising a deflectable cap affixed to the interior of said front end of said body, said cap being subject to deflection by said head portion of said plunger assembly as said outwardly facing circumferential groove approaches said inwardly facing circumferential groove, such that an administrator of an injection will sense a change in the action of said syringe and know that slight further movement of said rod member toward said front end will bring said grooves into radial alignment.

* * * * *